(12) United States Patent
Milgramm et al.

(10) Patent No.: US 7,574,254 B2
(45) Date of Patent: *Aug. 11, 2009

(54) METHOD FOR MONITORING ATTENTIVENESS AND PRODUCTIVITY IN A SUBJECT

(75) Inventors: Michael Milgramm, Valley Stream, NY (US); Alex Imas, Niles, IL (US)

(73) Assignee: WaveSynch Technologies, Inc., Forest Hills, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/270,620

(22) Filed: Nov. 13, 2008

(65) Prior Publication Data

US 2009/0124921 A1    May 14, 2009

Related U.S. Application Data

(60) Provisional application No. 60/987,606, filed on Nov. 13, 2007.

(51) Int. Cl.
*A61B 5/00* (2006.01)
(52) U.S. Cl. ....................... 600/544; 600/300
(58) Field of Classification Search ........................ None
See application file for complete search history.

(56) References Cited

U.S. PATENT DOCUMENTS

| 5,137,027 | A | 8/1992 | Rosenfeld |
| 5,267,570 | A | 12/1993 | Preston |
| 5,295,491 | A | 3/1994 | Gevins |
| 5,447,166 | A | 9/1995 | Gevins |
| 5,724,987 | A | 3/1998 | Gevins |
| 5,816,247 | A | 10/1998 | Maynard |
| 6,070,098 | A | 5/2000 | Moore-Ede |
| 6,272,378 | B1 | 8/2001 | Baumgart-Schmitt |

(Continued)

FOREIGN PATENT DOCUMENTS

WO    WO 2006/000166    1/2006

OTHER PUBLICATIONS

Makeig, S. et al., Lapses in Alertness: Coherence of Fluctuation in Performance and EEG Spectrum, Electroencephalography and Clinical Neurophysiology, v86 p. 23-25 (1993).

(Continued)

*Primary Examiner*—Robert L Nasser
(74) *Attorney, Agent, or Firm*—Gary J. Gershik; Cooper & Dunham LLP (57) ABSTRACT

This invention provides an EEG-based method of determining whether a test subject is sufficiently alert to perform a predefined task. The non-invasive method permits continuous monitoring of the individual's EEG signal, producing a set of real time frequency bands that indicate their state of wakefulness. When the frequency bands begin to skew towards the lower end, indicating the onset of drowsiness and eventual sleep, the system optionally sounds an acute alarm tone to alert the individual back to attention. The method also provides remotely monitoring the alertness of an individual and can be used, for example, to monitor productivity. In addition, the technology monitors self-recognized errors through the utilization of the ERN waveform. The remote or in-person monitoring can be continuous for any period of time.

20 Claims, 7 Drawing Sheets

U.S. PATENT DOCUMENTS

| | | | |
|---|---|---|---|
| 6,496,724 | B1 | 12/2002 | Levendowski et al. |
| 6,511,424 | B1 | 1/2003 | Moore-Ede |
| 6,625,485 | B2 | 9/2003 | Levendowski et al. |
| 6,754,524 | B2 | 6/2004 | Johnson |
| 2002/0186921 | A1 | 12/2002 | Schumacher |
| 2004/0044293 | A1 | 3/2004 | Burton |
| 2005/0017870 | A1 | 1/2005 | Allison et al. |
| 2008/0177197 | A1 | 7/2008 | Lee et al. |

OTHER PUBLICATIONS

Papadelis C., et al., Monitoring sleepiness with on-board electrophysiological recordings for preventing sleep-deprived traffic accidents, Clinical Neurophysiology (Ireland), p. 118/9 (Sep. 1, 2007).

Kaplan, Richard Drederic, An Innovative EEG Based Approach to Drowsiness Detection, vol. 6005B of Dissertation Abstract International, pp. 2319 (1996).

Fernandez, Thalia, et al., Incorrect performance and lower EEG frequency in specific areas, Electroencephalography and Clinical Neurophysiology, vol. 103, Issue 1, p. 218 (Jul. 1997).

Lal, Saroj K. L. et al., Development of an algorithm for an EEG-based driver fatigue countermeasure, Journal of Safety Research, vol. 34, Issue 3, pp. 321-328 (Aug. 2003).

Murphy, Timothy I. et al., The effect of sleepiness on performance monitoring: I know what I am doing, but do I care?, Journal of Sleep Research, vol. 15, Issue 1, pp. 15-21 (Feb. 20, 1996).

Lafrance, et al., Diurnal variations in the waking EEG: comparisons with sleep latencies and subjective alertness, Journal of Sleep Research, vol. 9, No. 3, pp. 243-248 (Sep. 2000).

Jung, Tzyy-Ping, et al., Estimating alertness from the EEG power spectrum, Eiomedical Engineering, vol. 44, Issue 1, p. 60-69 (Jan. 1997).

Makeig, Scott, et al., Changes in alertness are a principal component of varience in the EEG spectrum, Neuroreport, vol. 7, Issue 1, p. 213-216 (Dec. 29, 1995).

Lal, Saroj K.L. et al., Driver fatigue: Electroencephalography and psychological assessment, Psychophysiology, p. 313-321 (2002).

Makeig, S. et al., Lapses in Alertness: Coherence of Fluctuation in Performance and EEG Spectrum, Electroencephalography and Clinical Neurophysiology, v86 p. 23-25 (1993).

International Search Report issued Jan. 30, 2009 in connection with the counterpart PCT International Application No. PCT/US2008/012810.

METHOD FOR MONITORING ATTENTIVENESS AND PRODUCTIVITY IN A SUBJECT

This application claims benefit of U.S. Provisional Application No. 60/987,606, filed Nov. 13, 2007, the contents of which are hereby incorporated by reference.

BACKGROUND OF THE INVENTION

It is a commonly known fact that when one places two conducting electrodes connected to a voltmeter, one on the scalp and the other on an electrically neutral area, such as the mastoids behind the ears, a quantifiable voltage can be observed. This voltage signal and its change with respect to time is the basis of electroencephalography, or EEG. The signal measured on the scalp is actually a summation of individual postsynaptic potentials occurring within the brain. Since both the neural tissue and the skull act as a low pass filter, it is unlikely that the high frequency transients of action potentials would make it up to the scalp, and since postsynaptic potentials generally have lower frequency transients associated with them, it is widely believed that the observed EEG signal originates from them.

The EEG recording is characterized by amplitude, frequency and their change over time. The frequency component of the EEG can be utilized to infer the level of an individual's neural activity. The frequencies are broken down into ranges which describe how alert and conscious a person is at any given time. The delta frequency (1-4 Hz) is associated with deep sleep. The theta frequency (5-7 Hz) is associated with drowsiness, and delta activity is also common. The alpha frequency (8-13 Hz) is associated with relaxed wakefulness, where not much brain resources are devoted to any one thing. The beta frequency (12-20 Hz, or 30 Hz) and the gamma frequency (36-44 Hz) are associated with alert attentiveness.

SUMMARY OF THE INVENTION

A method of monitoring productivity and determining whether a test subject is sufficiently alert to perform a predefined task comprising:

a) recording an electroencephalograph (EEG) over a period of time from the test subject using an EEG recording apparatus;

b) analyzing the frequency distribution of the wavebands recorded in the EEG; and c) quantitating any ERN (error related negativity) waveform in the EEG, wherein presence in the EEG of both (1) (a) an alpha waveband power component ratio of 0.5-1.0 and a theta waveband power component ratio of less than 0.5 or (b) a theta waveband power ratio of 0.5-1.0 and an alpha waveband power component ratio of less than 0.5; and (2) one or more ERN waveforms recorded during the period of time indicates that the test subject is not sufficiently alert to perform the predefined task, and wherein the presence of (1) but not (2), or (2) but not (1), indicates that the test subject is sufficiently alert to perform a predefined task.

DETAILED DESCRIPTION OF THE INVENTION

A method of determining whether a test subject is sufficiently alert to perform a predefined task comprising:

a) recording an electroencephalograph (EEG) over a period of time from the test subject using an EEG recording apparatus;

b) analyzing the frequency distribution of the wavebands recorded in the EEG; and c) quantitating any ERN (error related negativity) waveform in the EEG, wherein presence in the EEG of both (1) (a) an alpha waveband power component ratio of 0.5-1.0 and a theta waveband power component ratio of less than 0.5 or (b) a theta waveband power ratio of 0.5-1.0 and an alpha waveband power component ratio of less than 0.5; and (2) one or more ERN waveforms recorded during the period of time indicates that the test subject is not sufficiently alert to perform the predefined task, and wherein the presence of (1) but not (2), or (2) but not (1), indicates that the test subject is sufficiently alert to perform a predefined task.

In embodiments of the method steps b) and c) can be performed in any order, or simultaneously.

It is noted that the level of attentiveness to a task (alertness) and the incidence of ERNs when performing the task is related to the productivity of the subject with regard to that task. Thus, the method can be used to monitor a subject's productivity, including remote monitoring of a subject's productivity.

In an embodiment the EEG is recorded using at least two active electrodes each comprising an Ag—AgCl recording tip. In an embodiment one active electrode records from a Fz site on the test subject's head. In an embodiment the EEG is recorded using at least four active electrodes, with three recording from the Fz site on the test subject's head and one recording from a mastoid area of the test subject's head.

In an embodiment the method further comprises correcting the first and second EEG for test subject's eye blinks before step) or step c). In an embodiment the EEG is corrected for test subject's eye blinks as measured by a fiber-optic eye blink detector.

In an embodiment the theta waves have a frequency of 5-7 Hz, and the alpha waves have a frequency of 8-13 Hz.

In an embodiment the method further comprises alerting the test subject with an audible signal if the test subject is not sufficiently alert to perform the predefined task.

In an embodiment an incidence of 4 or more of ERN waveforms in the EEG must be recorded to indicate that the subject is not sufficiently alert to perform a predefined task.

In an embodiment the method effects monitoring productivity of a subject. In an embodiment, a higher ERN incidence and lower alertness than a control subject indicates that the subject has low productivity.

In an embodiment the period of time is 5, 10, 15, 20, 25 or 30 minutes. In an embodiment the period is between 30 minutes and 24 hours.

In an embodiment the ERN waveform(s) are detected in real time by performing a frequency transform of the EEG.

In an embodiment each EEG recording is sequentially (a) amplified; (b) filtered through a 30 Hz low pass filter and a 0.3 Hz high pass filter; (c) converted from analog to digital; (d) subjected to a fast Fourier transform.

In an embodiment the EEC is denoised prior to step b).

In an embodiment the alpha waveband power component ratio is 0.5-1.0 and the theta waveband power component ratio is less than 0.5.

In an embodiment the theta waveband power ratio is 0.5-1.0 and the alpha waveband power component ratio is less than 0.5.

In regard to the power component ratio, a frequency band power is computed through a Power Spectrum Analysis (PSA) wherein a Fast Fourier Transform (FFT) is applied to the raw EEG signal and a power spectrum is computed ($\mu V^2/Hz$). The spectrum is then condensed and analyzed into frequency bands divided into delta (1-4 Hz), theta (4-8 Hz), alpha (8-12 Hz) and beta (12-20 Hz) components. Power component ratios are then determined by dividing the power of the particular frequency band by the sum of the powers of all of the recited frequency bands. Thus an alpha power component ratio would be: Alpha power/(delta power+theta power+alpha power+beta power).

In embodiments the alpha waveband power component ratio is 0.5, 0.55, 0.6, 0.65, 0.7, 0.75, 0.8, 0.85, 0.9, 0.95, or 1.0, or any range thereof, when the theta waveband power component ratio is less than 0.5.

In embodiments the theta waveband power component ratio is 0.5, 0.55, 0.6, 0.65, 0.7, 0.75, 0.8, 0.85, 0.9, 0.95, or 1.0, or any range thereof, when the alpha waveband power component ratio is less than 0.5.

Where a range is give it is understood that the range includes all integers and 0.1 units within that range, and any sub-range thereof. For example, a range of 30 minutes to 24 hours includes the times 31 minutes, 32 minutes etc., as well as the ranges 45 minutes to 55 minutes, 44 minutes to 59 minutes, etc.

The monitoring of the EEG can be done in-person, in proximity, or performed remotely. For example, the EEG can be recorded locally and the information, or alternatively the analyzed information, can be transmitted to a remote location for an observer.

Every embodiment described herein may be performed employing a computer and associated relevant apparatus as described herein.

All combinations of the various elements described herein are within the scope of the invention.

EXPERIMENTAL DETAILS

EEG recording and the apparatus that may be used therefor are described in Allison et al., U.S. Patent Application Publication No. 2005/0017870; Preston, U.S. Pat. No. 5,267,570; Gevins, U.S. Pat. No. 5,724,987; Gevins, U.S. Pat. No. 5,447,166; Gevins, U.S. Pat. No. 5,295,491; Maynard, U.S. Pat. No. 5,816,247; Burton, U.S. Patent Application Publication No. 2004/0044293; Levendowski et al., U.S. Pat. No. 6,625,485; Levendowski et al., U.S. Pat. No. 6,496,724; Johnson, U.S. Pat. No. 6,754,524; Moore-Ede, U.S. Pat. No. 6,511,424; Moore-Ede, U.S. Pat. No. 6,070,098; and Pavelka., WO 2006/000166, each of which is hereby incorporated by reference.

Traditionally, an EEG was recorded using hollow disk electrodes made from tin, silver or gold. The electrodes were attached to the subject's scalp using conduction paste in order to minimize noise and impedance of the signal. The subject's scalp had to be prepared by cleansing the areas involved in the experiment usually through abrasion. Recently, a new type of electrode has been developed that functions through an active setup. The electrode is able to tolerate high levels of impedance and consequently prior skin preparation is no longer necessary. The new electrode, available as for example the BioSemi Pin-Type active electrode, contains an Ag—AgCl tip which eliminates most noise and significantly lowers signal impedance. The electrode is fitted into specially designed holders on the BioSemi headcap which are filled with electrode gel through a syringe. The elastic headcap is then fitted atop the subjects head and the EEG data collection can begin. The technology disclosed herein can employ the active electrode setup so as to minimize time and participant discomfort. After the electrode holders are filled with gel and the appropriate electrodes are attached, the electroencephalogram of many individuals can be obtained without any further setup. The individual in charge of running the biometric technology replaces the electrode gel as needed.

In order to record EEG, a minimum of two electrodes is necessary. One electrode must be placed at the reference point and another at the site of interest. The reference point should be electrically neutral so as to act as a baseline (different from the pre-signal baseline used to measure ERPs) which coupled with the signal from the electrode on the scalp will be used to calculate the EEG voltage potential readings. Typically the mastoids or the ears are used as the reference point: the mastoids being well insulated by a particularly thick layer of bone to impede the signal and the ears being far enough from the signal source to pick up anything substantial.

The EEG signal can be distorted by external noise signals which have a variety of sources. The source of noise that would most significantly affect the technology is blinking. When an individual blinks it causes a significant jump in the voltage potential that may be interpreted as an event related potential. Several techniques have been developed to eliminate the influence of this artifact. Many practitioners apply two additional electrodes for electrooculography (EOG) recording diagonally above and below the eye to pick up vertical and horizontal eye movements. When the voltage potential from those two electrodes exceeds a certain threshold, over 80 $\mu V$ in most protocols, that particular trial is disregarded as containing an artifact so that only error-free trials are kept. This is accomplished through a program, introduced by Gratton, Coles and Donchin in 1983 and further developed by Ziegler and Gattaz in 1992, which determines the magnitude of correlation between eye electrodes' vertical and horizontal leads and the EEG signal. For the purposes of the technology described here, the number of electrodes necessary for EEG recording can be minimized by an eye sensor that detects blinks, such as the Fiber-Optic Eye-Blink Switch (PSSW-EB), that is used to detect blinks and then signal for the EEG recording program to eliminate those trials. This will eliminate the need for EOG recording.

Figure 1:
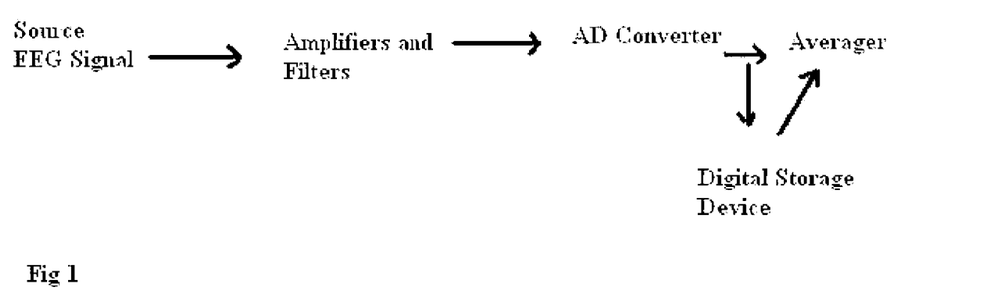
FIG. 1: Process for collecting EEG information.

FIG. 1 describes the path of the raw EEG signal as it is converted into a form that is usable for analytical purposes. The signal is first passed through amplifying and filtering systems which increase the strength of the signal, accentuate the desired portions and filter out any unwanted frequencies. The gain should be set high enough so that the amplitude is sufficiently sensitive to pick up small deflections, but low enough so that saturation or clipping does not occur. The filtering system should couple a low pass and high pass filter in order to control for noise or artifacts. A typical protocol for recording P300 ERPs sets the low pass filter at 30 Hz and the high pass filter at 0.3 Hz (Rosenfeld et al 2003). The modified signal is then sent to an Analog to Digital Converter (A/D Converter) which samples the analog signal, typically at 100

Hz, and converts the data into a digital stream. The EEG recording is now usable for software analysis. Applying a Fast Fourier Transform (FFT) at this point decomposes the complex signal into its underlying sine wave constituents, and a frequency band diagram can be composed that illustrates the prominence of different frequencies in the subject's EEG recording.

An electroencephalogram can be decomposed into frequency bands which could then be analyzed to determine the person's attentive state. For example, if a person showing up to work with bands more skewed towards the theta/alpha range, it is likely that the individual is still drowsy and will not be able to work efficiently (depending on the job of course) for some time. On the other hand if the worker had bands skewed more towards the beta/gamma range, then it can inferred that the individual is capable of delving immediately into the work schedule.

Event Related Potential:

For the purposes of the technology disclosed here a particular component is analyzed of the EEG called the Event Related Potential (ERP). Essentially, the ERP is the body's psychophysiological response to a given stimulus. Since individual neurons have relatively little electrical activity associated with them, certainly not enough to be detected on the scalp, ERPs are recorded when neurons act synchronously and the electric fields generated by each particular neuron are oriented in such a way that the effects on the scalp cumulate. Only neurons organized in a layered open field manner (neurons with dendrites and axons oriented in the same fashion) are picked up as an ERP. Given that property, an infinite amount of generators in different parts of the brain can be producing the ERP; just because an ERP is detected in a certain place on the scalp does not mean that it is being generated from a single area within the brain—you can infer location of surface activity but not internal activity. Stimuli that cause ERPs can either be external, such as the memory coupled stimulus that invokes the P300, or internal, such as the rhythmic pacemaker-like oscillations projected by the nucleus reticularis to thalamic nuclei and the cortex.

Figure 2:
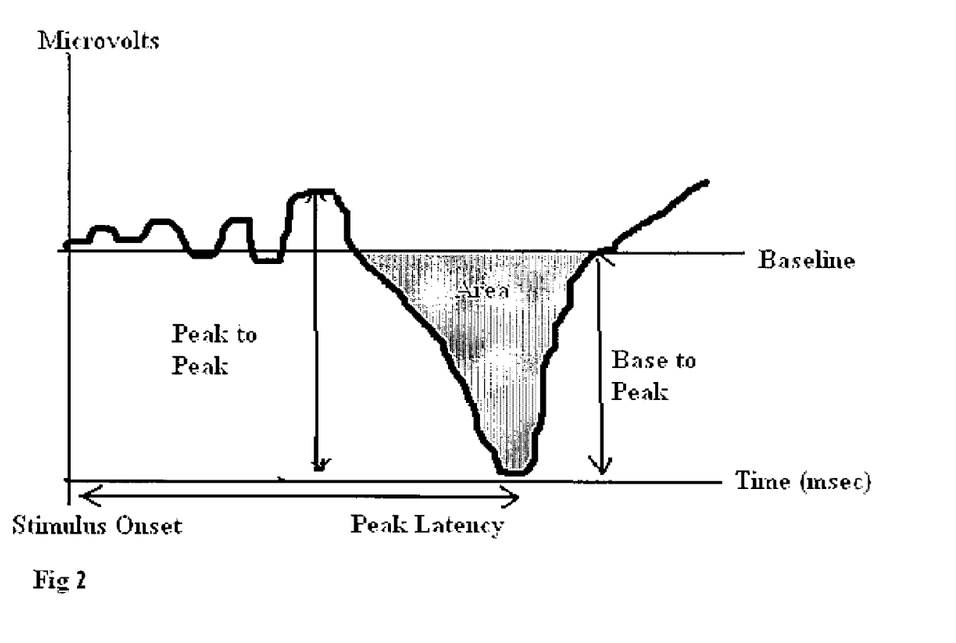
FIG. 2: An Event Related Potential—the P300 waveform

ERPs are generally small, about 50 µV, in comparison to the overall EEG recording. Hence, in order to perform an analysis on it the discrimination of the signal must be increased from the background noise of the general EEG. In order to accomplish this, the EEG recording is sent to the Averager. In order to average out the EEG noise, the ERP signal must be constant over trials, the noise must be random across trials and the ERP signal must be independent of background noise. Therefore, because the ERP signal is time locked, the EEG background noise can be averaged out leaving only the desired ERP signal. The number of samples used in the average is related to the signal to noise ratio, so a minimum of 20 samples must be used to produce a viable ERP. The result is a voltage vs. time function containing a number of positive and negative peaks. ERPs are described in terms of their characteristic scalp distribution, polarity and latency; a typical ERP readout (in this case the P300) is pictured in FIG. 2. ERNs are another type of ERP.

The technology disclosed here records the incidence and frequency of subject-recognized errors through the utilization of the ERN waveform. The ERN is a negative waveform that is observed when subjects make a mistake. The ERN is a response-locked ERP at fronto-central recording sites is characterized by a negative deflection that peaks approximately 50 ms post-response (Falkenstein et al., 2000). Incorporating the monitoring for this ERP into the alertness technology requires that the recorded EEG signal be converted into time-frequency transforms. Using the principle component analysis (PCA) approach to time-frequency transforms (TFT's) allows for the real time monitoring for ERN occurrences. The EEG signal would be converted to TFT's, a frequency pattern of the ERP we are looking for (ERN in our case) would be determined, and so whenever that frequency pattern is detected, the ERP can be detected in real time despite the fact that the ERP is stimulus locked. No averages are necessary to detect it and consequently the technology will be able to detect self-recognized errors while monitoring the user's state of alertness.

The non invasive system continuously monitors the individual's EEG signal, producing a set of real time frequency bands that indicate their state of wakefulness. When the frequency bands begin to skew towards the lower end, indicating the onset of drowsiness and eventual sleep, the system sounds an acute alarm tone to alert the individual back to attention. The alertness level of the individual can also be monitored remotely. In addition, the technology monitors self-recognized errors through the utilization of the ERN waveform. Whenever a user recognizes that he has made an error, the technology records the resulting ERN waveform and documents it in the user's logs.

Figure 3:
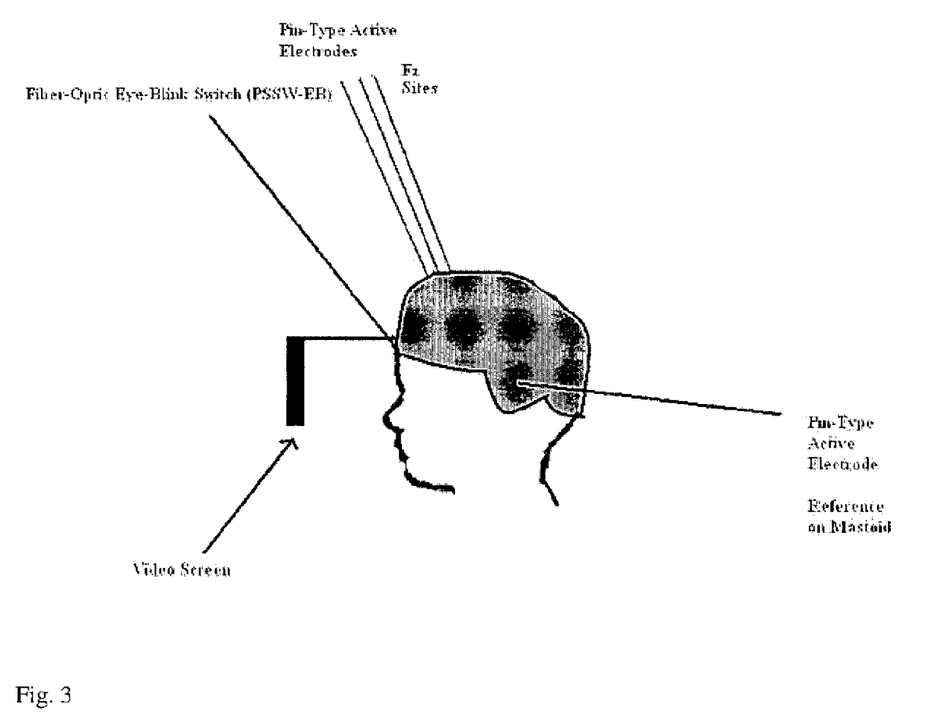
FIG. 3: Pin electrode EEG headcap device (with fiber optic blink switch), with optional video screen attachment.
Figure 4:
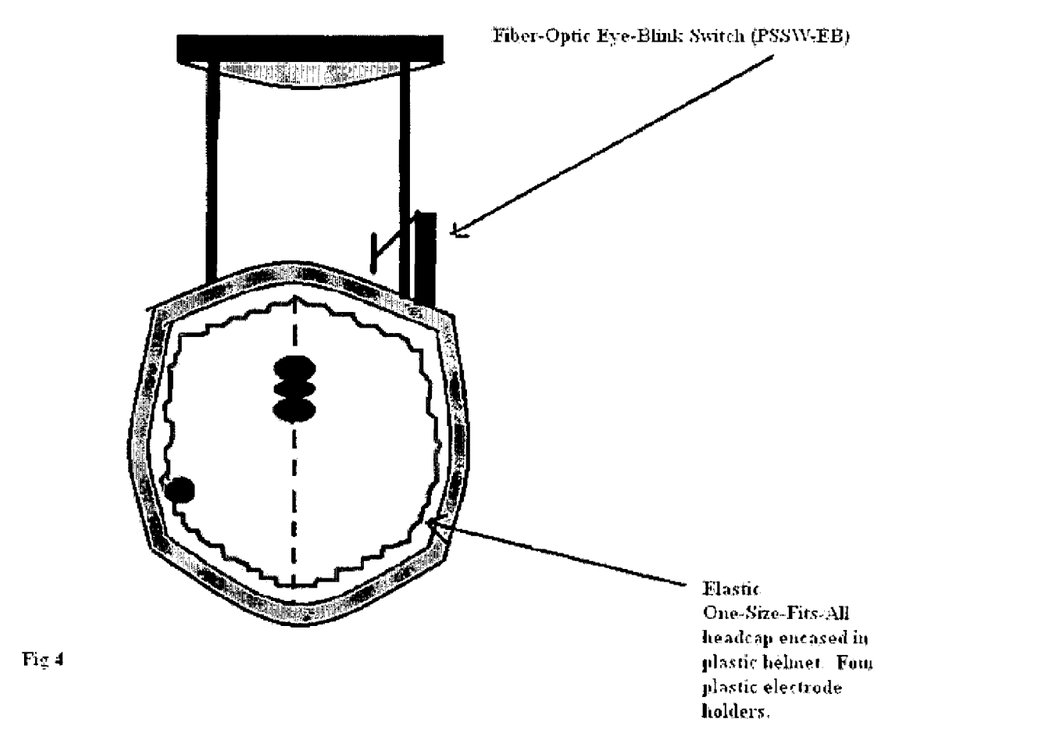
FIG. 4: Top view of Pin electrode EEG headcap device (with fiber optic blink switch), with optional video screen attachment.

The elements that receive and modify the raw EEG signal can be effectively implemented in the current state. The technology that collects the actual EEG signal on the other hand can be modified in order to meet the requirements mentioned above. A design for such device is depicted in FIGS. 3 and 4.

Figure 5:
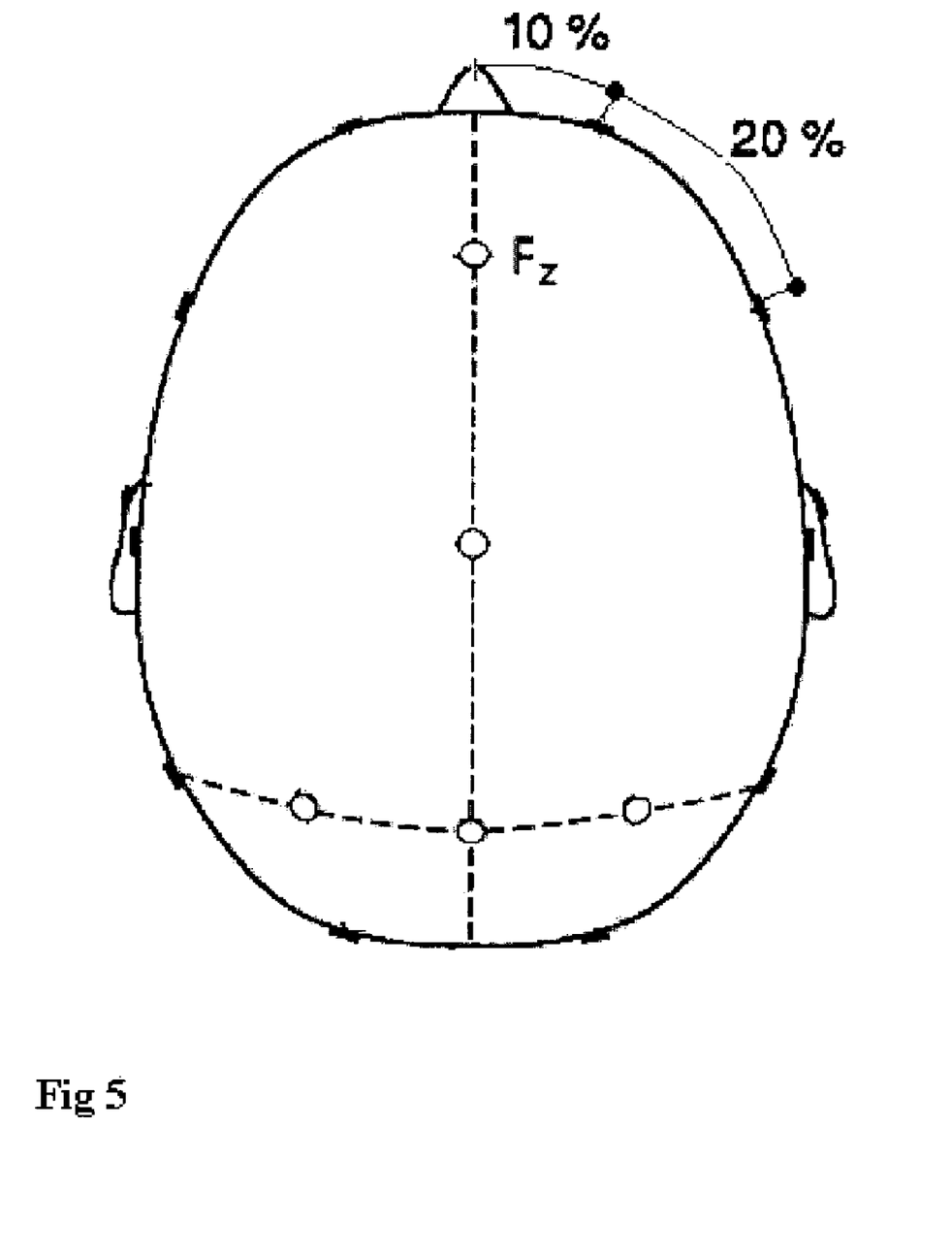
FIG. 5: Pz recording site.

The outside of the device consists of a plastic helmet measuring between 62-66 cm in circumference, able to fit most individuals since head circumferences typically range between 46-62 cm. The helmet has 4 holes for the electrode holders, allowing them to be filled periodically with electrical gel by the person who maintains it. As mentioned above, the use of active electrodes eliminates the need for scalp cleansing and therefore cuts the prep time for EEG recording to significantly nothing. The 3 electrode holders at the top of the helmet are meant for the recording Pz EEG signals. FIG. 5 shows the location of the Pz site on an individual's scalp.

Since typical head circumferences range between 46-62 cm, the 20% mark of the Pz site lies 6.9-9.3 cm from the vertical midline. Therefore, in order to insure that the EEG signal is being recorded from the Pz site of every individual, 3 electrodes are placed 6.9 cm, 8.1 cm and 9.3 cm from the vertical midline of the helmet, respectively. The signals from each electrode are then averaged to produce a single EEG recording. This allows the technology to be used on most individuals without having to worry about different sizes for the device.

The inside of the helmet contains an elastic headcap, similar to the one designed by BioSemi, to which the electrode holders are actually attached. It will comfortably fit on the heads of most individuals and allow for maximal proximity of the electrodes to the scalp. A Fiber Optic Eye Blink Switch attached to the front of the helmet will detect blinks and signal the recording software to eliminate the implicated trials. This eliminates the need for EOG recording and makes the process of gathering data more comfortable for the individual because there are no electrodes or device protrusions touching his face. A video screen is attached to the front of the helmet and displays the appropriate visual stimuli. It works in conjunction with the EEG recording software and presents stimuli according to the conditions set by the individual running the technology. This makes the technology significantly more versatile in that it can be used in any space containing a personal computer and signal processing devices, such as a building lobby or an office.

The device is preferably used continuously to monitor an individual's state by measuring their frequency bands and ERN rate. As such the device can either alert the individual wearing it that they are becoming fatigued or to alert an external "monitor" (manager, HR department, supervisor) about the individual's well being. The ERN function is a measure of productivity (how many errors the individual is making) and the frequency band analysis is a measure of their attentiveness. Hence, this technology can either a) keep the individual attentive through an alarm device, or b) allow a supervisor to monitor this individual on a continual basis.

Figure 6:
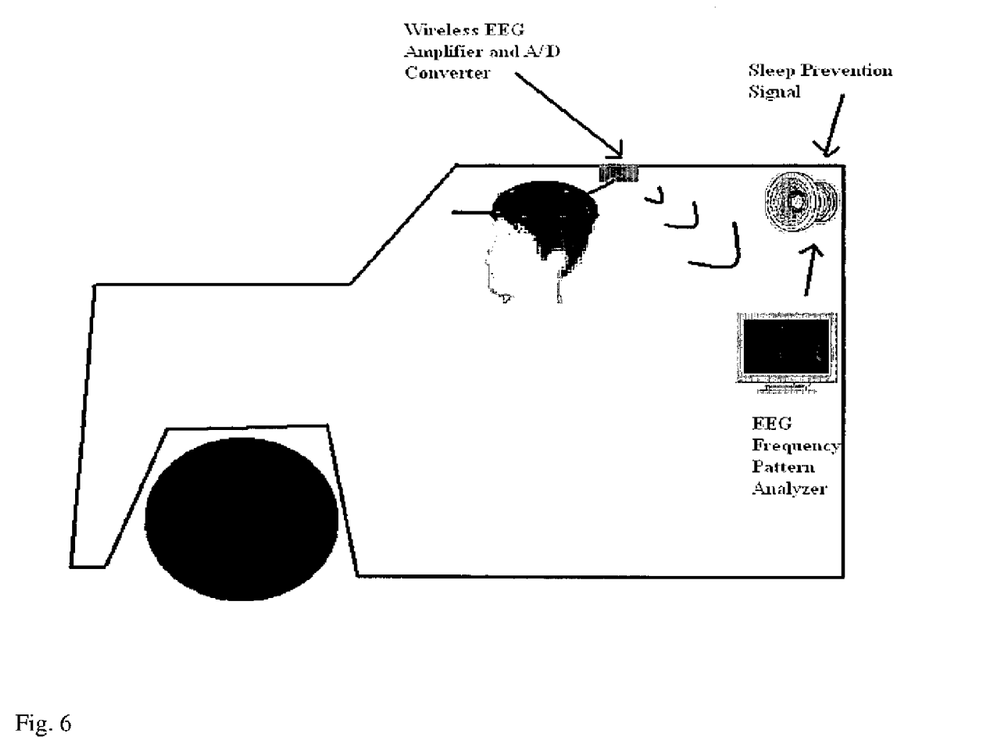
FIG. 6: EEG-based alertness system for driver.

The technology can be worn by truck drivers to monitor their alertness on the road. The EEG collection device used in this application can be the one depicted in FIGS. 3 and 4. Since it will be used to collect a more general EEG signal, the video screen and the hard plastic helmet would not be necessary. The elastic headcap with attached active electrodes would be connected to a battery powered EEG amplifier and A/D Converter, such as the Pocket A3 EEG/HEG Trainer developed by Minder Labs, attached to the roof of the vehicle. The elastic headcap itself can be placed within a variety of headgear from a modified baseball cap to the plastic helmet depicted in FIG. 4. The device would then send the now digitalized EEG signal to the EEG Frequency Pattern Analyzer which would use software such as BioExplorer to analyze the frequency pattern of the EEG signal. If the signal begins to skew towards the lower frequencies, such that the brain pattern consists of low level alpha, theta and delta waves, the technology would then send a indicator to a signaling device which would consequently produce a noise stimulus loud enough to wake up the dozing driver. One way of setting up the technology is depicted in FIG. 6.

Figure 7:
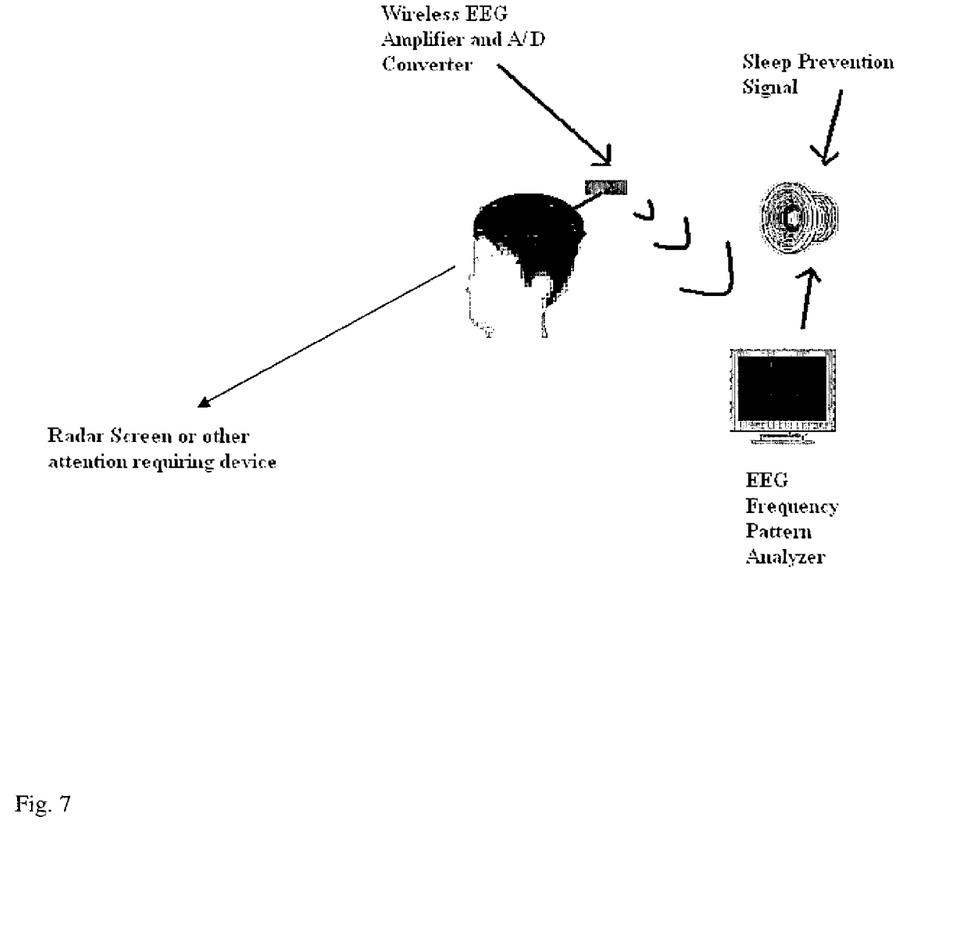
FIG. 7: EEG-based alertness system for person paying attention to task.

This technology can be used for those who have to carefully monitor a particular situation for extended periods of time. An example of this would be an employee (military, air traffic controller, nuclear power plant controller etc.) who has to monitor and analyze the computer screen, the radar screen for foreign flying objects for prolonged shifts of time while making sure to stay attentive to the task throughout. The device can be placed over the individual's head analogously to the method described above, and whenever the EEG signal begins to skew towards the lower frequency range an alarm would alert the individual back to the task at hand. One way of setting up the technology is depicted in FIG. 7.

EXAMPLES

An electroencephalograph (EEG) is recorded over a period of time from the test subject using an EEG recording apparatus. The EEG is analyzed for the frequency distribution of the wavebands and any waveform in the EEG is quantitated. The subject is found to have an alpha/beta wave ratio above the reference ratio and is observed to have an ERN in the EEG. The test subject is not sufficiently alert to perform the predefined task.

An electroencephalograph (EEG) is recorded over a period of time from the test subject using an EEG recording apparatus. The EEG is analyzed for the frequency distribution of the wavebands and any ERN waveform in the EEG is quantitated. The subject is found to have an alpha/beta wave ratio above the reference ratio but is not observed to have an ERN in the EEG. The test subject is sufficiently alert to perform the predefined task.

An electroencephalograph (EEG) is recorded over a period of time from the test subject using an EEG recording apparatus. The EEG is analyzed for the frequency distribution of the wavebands and any ERN waveform in the EEG is quantitated. The subject is found to have an alpha/beta wave ratio below the reference ratio but is not observed to have an ERN in the EEG. The test subject is sufficiently alert to perform the predefined task.

The examples are repeated wherein the EEG signal is sequentially (a) amplified; (b) filtered through a 30 Hz low pass filter and a 0.3 Hz high pass filter; (c) converted from analog to digital; (d) subjected to a fast fourier transform and then analyzed to determine the principal components by frequency.

What is claimed is:

1. A method of determining whether a test subject is sufficiently alert to perform a predefined task comprising:
    a) recording an electroencephalograph (EEG) over a period of time from the test subject using an EEG recording apparatus;
    b) analyzing the frequency distribution of the wavebands recorded in the EEG; and
    c) quantitating any ERN waveform in the EEG,
wherein presence in the EEG of both (1) (a) an alpha waveband power component ratio of 0.5-1.0 and a theta waveband power component ratio of less than 0.5 or (b) a theta waveband power ratio of 0.5-1.0 and an alpha waveband power component ratio of less than 0.5; and (2) one or more ERN waveforms recorded during the period of time indicates that the test subject is not sufficiently alert to perform the predefined task, and wherein the presence of (1) but not (2), or (2) but not (1), indicates that the test subject is sufficiently alert to perform a predefined task.

2. The method of claim 1, wherein steps b) and c) can be preformed in any order.

3. The method of claim 1, wherein steps b) and c) are performed simultaneously.

4. The method of claim 1, wherein the EEG is recorded using at least two active electrodes each comprising an Ag—AgCl recording tip.

5. The method of claim 4, wherein one active electrode records from a Fz site on the test subject's head.

6. The method of claim 5, wherein the EEG is recorded using at least four active electrodes, with three recording from the Fz site on the test subject's head and one recording from a mastoid area of the test subject's head.

7. The method of claim 1, further comprising correcting the first and second EEG for test subject's eye blinks before step) or step c).

8. The method of claim 7, wherein the EEG is collected for test subject's eye blinks as measured by a fiber-optic eye blink detector.

9. The method of claim 1, wherein the theta waves have a frequency of 5-7 Hz, and the alpha waves have a frequency of 8-13 Hz.

10. The method of claim 1, further comprising alerting the test subject with an audible signal if the test subject is not sufficiently alert to perform the predefined task.

11. The method of claim 1, wherein an incidence of 4 or more of ERN waveforms in the EEG must be recorded to indicate that the subject is not sufficiently alert to perform a predefined task.

12. The method of claim 1, wherein the method effects monitoring productivity of the subject.

13. The method of claim 1 wherein the ERN waveform(s) are detected in real time by performing a frequency transform of the EEG.

14. The method of claim 1, wherein each EEG recording is sequentially (a) amplified; (b) filtered through a 30 Hz low pass filter and a 0.3 Hz high pass filter; (c) converted from analog to digital; (d) subjected to a fast Fourier transform.

15. The method of claim 1, wherein the EEG is denoised prior to step b).

16. The method of claim 1, wherein the alpha waveband power component ratio is 0.5-1.0 and the theta waveband power component ratio is less than 0.5.

17. The method of claim 1, wherein the theta waveband power ratio is 0.5-1.0 and the alpha waveband power component ratio is less than 0.5.

18. The method of claim 1, wherein the period of time is 5, 10, 15, 20, 25 or 30 minutes.

19. The method of claim 1, wherein the period is between 30 minutes and 24 hours.

20. The method of claim 1, wherein high ERN incidence and low alertness indicates that the subject has low productivity.

* * * * *